United States Patent
Pop

(10) Patent No.: US 9,066,818 B2
(45) Date of Patent: Jun. 30, 2015

(54) SYSTEM COMPRISING AT LEAST ONE ORTHOPEDIC DEVICE AND A REMOTE CONTROL UNIT

(75) Inventor: Constantin Pop, Ternitz (AT)

(73) Assignee: OTTO BOCK HEALTHCARE PRODUCTS GMBH, Wien (AT)

(*) Notice: Subject to any disclaimer, the term of this patent is extended or adjusted under 35 U.S.C. 154(b) by 460 days.

(21) Appl. No.: 13/509,254

(22) PCT Filed: Nov. 12, 2010

(86) PCT No.: PCT/EP2010/006890
§ 371 (c)(1),
(2), (4) Date: May 10, 2012

(87) PCT Pub. No.: WO2011/057789
PCT Pub. Date: May 19, 2011

(65) Prior Publication Data
US 2012/0313745 A1    Dec. 13, 2012

(30) Foreign Application Priority Data
Nov. 13, 2009    (DE) .......................... 10 2009 052 891

(51) Int. Cl.
G09B 21/00    (2006.01)
A61F 2/68    (2006.01)
(Continued)

(52) U.S. Cl.
CPC . *A61F 2/68* (2013.01); *A61G 7/018* (2013.01); *A61G 2007/0514* (2013.01); *A61F 4/00* (2013.01); *A61G 2007/0524* (2013.01); *A61G 2203/12* (2013.01); *A61F 2/64* (2013.01); *A61F 5/0102* (2013.01); *A61F 2002/5003* (2013.01);
(Continued)

(58) Field of Classification Search
CPC .............................. A61F 2/66; A61F 2002/701
USPC ...................................... 340/4.11; 623/24, 43
See application file for complete search history.

(56) References Cited

U.S. PATENT DOCUMENTS 5,252,102 A * 10/1993 Singer et al. .................... 623/24
7,431,737 B2 10/2008 Ragnarsdottir et al.
(Continued)

FOREIGN PATENT DOCUMENTS

DE    69415397 T2    5/1999
DE    10311189 A1    10/2004
(Continued)

OTHER PUBLICATIONS

PCT International Search Report for International Application No. PCT/EP2010/006890, mailed Mar. 8, 2011.

*Primary Examiner* — Jennifer Mehmood
*Assistant Examiner* — Rufus Point
(74) *Attorney, Agent, or Firm* — Holland & Hart

(57) ABSTRACT

The invention relates to a system comprising at least one orthopedic device having at least one joint (4) and a resistance device associated with the respective joint (4), a control device and an actuator being associated with said resistance device. The joint can be moved or the resistance can be adjusted against a bending and/or stretching movement via the actuator. The system further comprises a remote control unit (6) which is coupled to the control device and via which the resistance behavior can be varied, wherein data for the remote control unit (6) are stored in the orthopedic device, the remote control (6) can be configured with said data and the data are transmitted via a pairing process to the remote control unit (6).

20 Claims, 1 Drawing Sheet

(51) Int. Cl.
- *A61F 2/64* (2006.01)
- *A61F 5/01* (2006.01)
- *G08C 17/00* (2006.01)
- *A61G 7/018* (2006.01)
- *A61G 7/05* (2006.01)
- *A61F 4/00* (2006.01)
- *A61F 2/50* (2006.01)
- *A61F 2/70* (2006.01)

(52) U.S. Cl.
CPC ... *A61F 2002/6818* (2013.01); *A61F 2002/705* (2013.01); *A61F 2002/707* (2013.01); *G08C 17/00* (2013.01); *G08C 2201/10* (2013.01); *G08C 2201/20* (2013.01); *G08C 2201/61* (2013.01)

(56) References Cited

U.S. PATENT DOCUMENTS

| | | | |
|---|---|---|---|
| 7,485,152 B2* | 2/2009 | Haynes et al. | 623/24 |
| 2003/0125814 A1 | 7/2003 | Paasivaara et al. | |
| 2004/0225242 A1* | 11/2004 | Lidolt et al. | 602/16 |
| 2005/0143589 A1* | 6/2005 | Donoghue et al. | 552/650 |
| 2005/0192677 A1* | 9/2005 | Ragnarsdottir et al. | 623/24 |
| 2006/0173552 A1* | 8/2006 | Roy | 623/24 |
| 2006/0195197 A1 | 8/2006 | Clausen et al. | |
| 2006/0253894 A1* | 11/2006 | Bookman et al. | 726/2 |
| 2007/0050044 A1* | 3/2007 | Haynes et al. | 623/24 |
| 2007/0083272 A1* | 4/2007 | Van De Veen et al. | 623/39 |
| 2007/0155588 A1* | 7/2007 | Stark et al. | 482/8 |
| 2008/0121701 A1* | 5/2008 | Gabriel | 235/382 |
| 2009/0016728 A1* | 1/2009 | Kindle | 398/106 |
| 2009/0030530 A1* | 1/2009 | Martin | 623/53 |
| 2009/0192619 A1* | 7/2009 | Martin et al. | 623/18.11 |
| 2010/0023133 A1* | 1/2010 | Fairbanks et al. | 623/24 |
| 2010/0082115 A1* | 4/2010 | Kapelke | 623/24 |
| 2010/0115279 A1* | 5/2010 | Frikart et al. | 713/171 |
| 2012/0078380 A1* | 3/2012 | Jonsson et al. | 623/24 |

FOREIGN PATENT DOCUMENTS

| | | |
|---|---|---|
| DE | 10351916 A1 | 6/2005 |
| DE | 60015384 T2 | 10/2005 |
| EP | 0628296 B1 | 12/1998 |
| EP | 1981012 A2 | 10/2008 |
| GB | 2280609 A | 2/1995 |
| WO | 2008033852 A2 | 3/2008 |

* cited by examiner

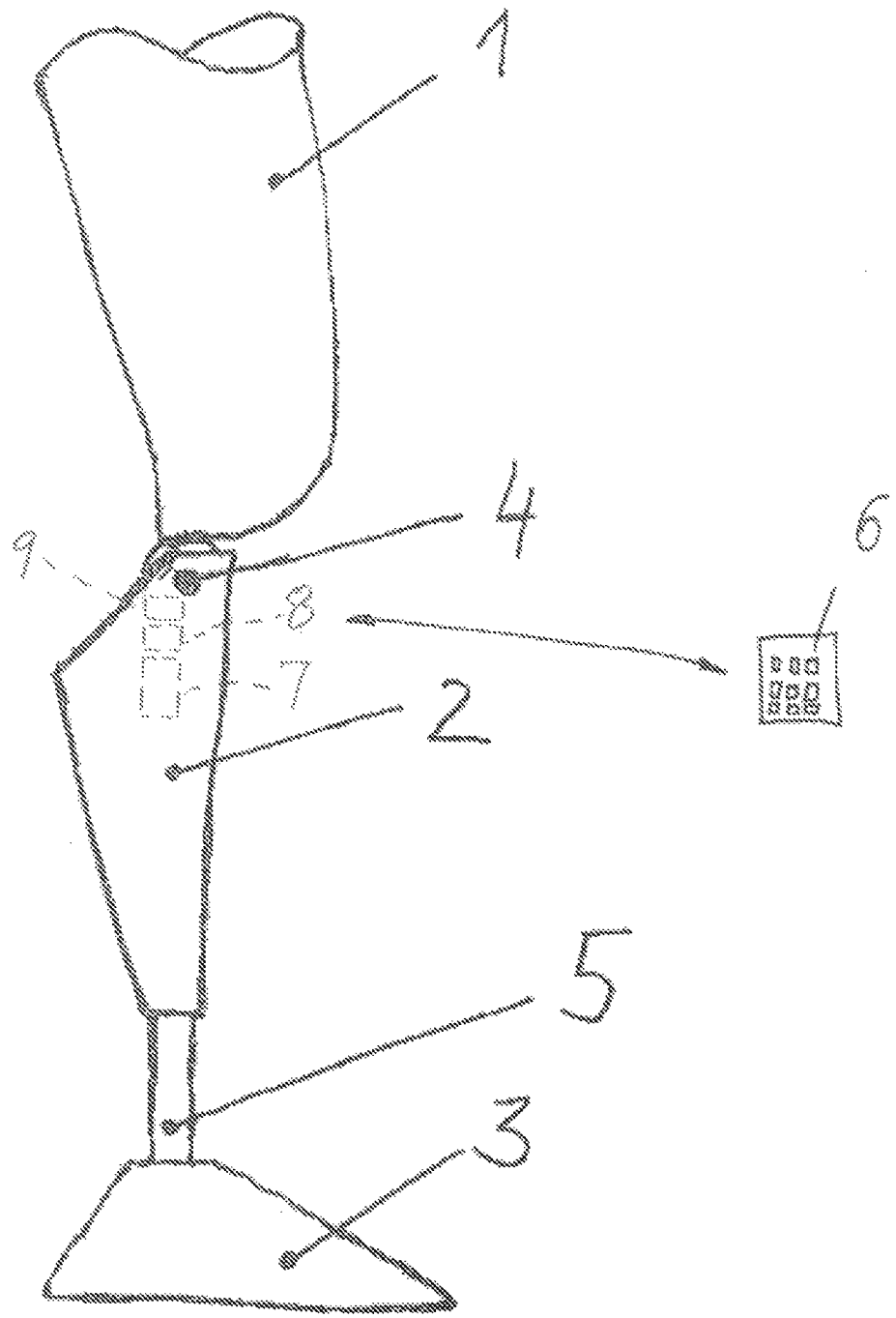

SYSTEM COMPRISING AT LEAST ONE ORTHOPEDIC DEVICE AND A REMOTE CONTROL UNIT

TECHNICAL FIELD

The invention relates to a system comprising at least one orthopedic device having at least one joint and a resistance device associated with the respective joint, a control device and an actuator being associated with said resistance device, wherein the joint is moved or the resistance to a bending and/or stretching movement can be adjusted via the actuator, and comprising a remote control unit, which is coupled to the control device and via which the resistance properties can be adjusted. Predominantly, such drives or electronically adjustable resistance devices are used in orthopedic devices for the lower extremities, in particular in prosthetic legs or leg orthoses, the adjustable resistance devices predominantly being used in prosthetic knee joints, prosthetic hip joints and prosthetic foot joints. In principle, however, provision is also made for prosthetics or orthoses on upper extremities to be equipped with corresponding systems, in addition to their use in prosthetic and orthotic devices for lower extremities.

BACKGROUND

DE 103 51 916 A1 has disclosed a prosthetic knee joint with an upper part and a lower part, which are pivotably connected to one another by a multiple-axis joint device. A resistance device is arranged between the upper part and the lower part, said resistance device providing this resistance to bending. In one configuration, a locking device for locking the prosthetic knee joint in the extended position is provided, wherein the locking device can be locked and unlocked by an actuating device. In order to facilitate operation, an actuating device which is driven via a remote control unit is provided.

DE 103 11 189 B4 describes an orthopedic aid with two parts capable of moving relative to one another and a locking apparatus for locking the two parts in a predetermined relative position and for unlocking the parts and for releasing the movement of the parts with respect to one another. The actuation of the locking apparatus can be performed by means of wireless transmission of an actuating signal.

DE 600 15 384 T2 describes a support apparatus which replaces the existence or the function of a limb and comprises at least two parts which are connected to one another by an artificial joint as well as a monitoring apparatus for the joint. The monitoring apparatus is arranged in such a way that it influences the joint on the basis of angle-of-inclination data. Before sitting down, the knee joint can be released by a special function, for example manually by a control means, such as a pushbutton fitted on the body or on The support apparatus, for example. The knee joint, remains released until the sensor indicates that an angle has decreased. down to a predetermined limit value.

SUMMARY

The object of the present invention is to provide a system with which it is possible for an orthopedic device to be matched safely and. flexibly to the requirements of the user.

According to the invention, this object is achieved by a system having the features of the main claim. Advantageous configurations and developments of the invention are given in the dependent claims.

The system according to the invention comprising at least one orthopedic device having at least one joint and a resistance device associated with the respective joint, a control device and an actuator being associated with said resistance device, wherein the joint is moved or the resistance to a bending and/or stretching movement can be adjusted via the actuator, and comprising a remote control unit, which is coupled to the control device and via which the resistance properties can be adjusted, provides that data for the remote control unit are stored in the orthopedic device, and said data can be used to configure the remote control unit and are transmitted to the remote control unit via a pairing process. Data relating to the parameters or control modes, for example, are stored in the orthopedic device, and in particular in the control device therein, wherein the data are provided for the remote control unit and the remote control unit can be coupled to the control device via a pairing process. It is thus possible for the remote control unit to not require any presetting as regards the respective parameters or control modes, but for the parameters, families of characteristics or else user interfaces of the respective control device, with assignment, are transmitted to the remote control unit.

The remote control unit and the orthopedic device are in this case matched to one another. Each joint with the respectively associated control device is coupled to the remote control unit and matched thereto in such a way that different data or control programs for the respective joints or control, devices can be transmitted individually to the remote control unit used. It is thus not necessary to provide special remote control units, possibly even a plurality of remote control units for an orthopedic device, but it is possible no control or adjust a large number of possibly even different orthopedic devices using a remote control unit which is only in principle pre-equipped. It is then possible, via the remote control unit, to adjust the time at which resistances are increased or decreased and/or to adjust an increase or decrease in resistances as such individually to the requirements of the respective user, for example. It is also possible to activate or deactivate operating modes. In this case, is goes without saying that the remote control unit also has a transmission device for transmitting signals to the orthopedic device, and this orthopedic device in turn receives the information items or signals by means of a reception device provided for this purpose. For simple transmission of the data from the orthopedic device, for example the prosthesis or orthosis, to the remote control unit, which is merely equipped with a basic structure and basic functionality, provision is made for a transmitter to be arranged in the orthopedic device and a receiver to be arranged in the remote control unit, via which wireless data transmission can take place. An additional possibility for data transmission can be provided by interfaces for data lines, with the result that the data can be transmitted between the remote control unit and the orthopedic device via a physical connection. The interfaces, generally jacks or plugs, can be provided as an alternative or in addition to the transmitter and the receiver.

Various control modes are stored in the control device, it being possible for said control modes to be activated and deactivated via the remote control unit. Each controller of an orthopedic device with a joint has a basic functionality, with which it is possible to run a standard movement program. In the case of prosthetic knees or knee orthoses, these are, for example, walking on a level and walking on slopes. If additional possibilities are intended to be provided in order to achieve matched control and matched drive or resistance properties, additional modes are activated, which are preferably stored in the control device in the orthopedic device. This makes it possible to provide an orthopedic device with a potentially complete program scope, of which only parts are enabled, however. In this case, the enabling takes place, for example, on the basis of physiological or therapeutic knowledge, with the result that it is possible to realize a different performance scope by means of different enabling of modes. By storing the modes in the respective control devices in the joints, it is possible to assign matched control programs to the respective joints, with the result that it is not necessary to equip a remote control unit with all possible control modes.

Preferably, data relating to the control parameters, control modes, language, arrangement of buttons, key assignments and/or adjustment ranges are stored in the orthopedic device, with the result that it is possible to configure the remote control unit with and with respect to the orthopedic device. The data required for this purpose are stored on the orthopedic device and are transmitted to the remote control unit. After the pairing process, in which the remote control unit is matched to the orthosis or prosthetic, the remote control unit has the data material required thereby in order to be able to adjust the prosthetic or orthosis within the scope of the acknowledged rights. The sequence in which which mode appears on the remote control unit, in what context parameters of the controller can be adjusted, how many modes can be adjusted, whether functions can be enabled and which keys have which functions can be stored on the orthosis or prosthetic. A mode is understood to mean a control response which can be switched on and off arbitrarily, while a function is in principle present and in particular controls safety-relevant processes and ensures the basic functionality. The adjustment possibilities are also defined via the transmitted data, i.e. how far the adjustment by the user of the remote control unit can go. The adjustment rights are limited in comparison with an orthopedic technician who generally changes the controller via a separate. interface.

The orthopedic technician can then configure the data which are later transmitted to the remote control unit via this separate interface, for example. For example, said orthopedic technician can define the nature, sequence, names and number of the additional modes and transmit the menu language for the remote control unit to the orthopedic device.

Furthermore, provision is made for the remote control unit to he capable of addressing a plurality of possibly different control devices, joints or else orthopedic devices collectively. It is possible for different joint devices on a user or patient to he driven, and it is likewise possible for identical devices on different patients to be addressed. Joint devices for knees, feet, hands, elbows or hips on a person can be driven in the same way as a plurality of joint devices which are each associated with only one joint type. This is advantageous in particular for orthopedic technicians since a large number of patients with a large number of different orthopedic devices can be supervised, using only one remote control unit. If a control module for a plurality of joint devices is provided in an orthopedic device, for example in the form of a central computation unit, the assignment within the remote control unit can easily take place via identification. In the case of a plurality of control devices, provision is advantageously made for the control devices on an orthopedic device to have a common basic identification which is supplemented by an identification for the respective joint, or the respective control device or the respective control program. The remote control unit can be designed to switch over between a plurality of control modes and/or enable control modes, wherein enabling means that a certain mode is activated when, for example, certain boundary conditions or movement states are detected via sensors. Switching over means that the respectively selected program or the selected mode is available at present and needs to be implemented. The activation or deactivation makes the respective mode effective.

Via the remote control unit it is possible to switch the control device into a deep-sleep mode and then possibly to withdraw it from this deep-sleep mode. The control device can be run up cyclically in the deep-sleep mode, for example, and check whether new signals from the remote control unit are present. If this is the case, the deep-sleep mode is ended and the control device is fully activated. It is likewise possible for the remote control unit to transmit a cyclic inquiry to the control device as to whether changes in the orthopedic device have taken place. Should this be the case, the deep-sleep mode is ended and the control device is fully activated.

A development of the invention envisages that a user identification is assigned to the remote control unit and is used to define which parameters and/or to what extent parameters can be adjusted in user-dependent fashion. Each user is provided with an identification. The user identification makes it possible for the respective user of a remote control unit to be provided with defined rights which can change parameters for the controller for the resistance device and which cannot. Provision is likewise made for rights as regards the scope of change of the parameters to be assigned. to the respective user, with the result that user-dependent adjustment of the parameters and therefore also of the control programs can take place. It is possible, for example, for an orthopedic technician to be provided with substantially more extensive change options in the controller than the user of the orthopedic device, since it can be assumed that an orthopedic technician, owing to his extensive training, can implement necessary changes for adapting the control properties to a greater extent than the end user. Such basic changes can be made on the basis of movement investigations and movement observations, and it is likewise possible for changed control modes to be matched to the changing movement sequence, for example within the realms of healing processes or adaptation processes. The end user, on the other hand, only has restricted adjustment possibilities via the remote control unit in order to be able to match the control to the individual requirements.

The user identification can be in the form of a code which can be input, for example, for example a numerical code, an alphanumerical code or another code. In this case, the individual user is in this case provided with a different code than, for example, the orthopedic technician or the programmer within the company manufacturing the orthopedic device. It is then possible, by means of the code, to establish in the pairing process which rights have been assigned to the respective user of the remote control unit, with the result that the adjustability is enabled within the predetermined framework as regards the nature and scope of the parameters to be adjusted. As an alternative or in addition, provision is made for the remote control unit to have a detection device for biometric data, via which a user identification is assigned. The biometric data identification device can be, for example, a fingerprint, scanner, but likewise other biometric data can be stored in the remote control unit in order to achieve individual, assignment.

BRIEF DESCRIPTION OF THE DRAWINGS

An exemplary embodiment of the invention will be explained in more detail below with reference to the attached figure, in which:

FIG. 1 shows a side view of a prosthetic in accordance with the present disclosure.

DETAILED DESCRIPTION

FIG. 1 shows a prosthetic with an upper limb shank 1 and a lower limb shank 2, which are connected to one another in articulated fashion via a prosthetic knee joint 4. A control device 7 is accommodated in the lower limb shank 2 for a resistance device 8, which is likewise arranged in the lower limb shank 2. An actuator 9 is associated with the resistance device 8. The prosthetic knee joint 4 is moved or the resistance to a bending and/or stretching movement can be adjusted via the actuator 9. A prosthetic foot 4 is fitted to the distal end of the lower limb part 2 and connected to the lower limb part 2 via a connecting shank 5.

The control device 7 is connected to a remote control unit 6 via a bidirectional communications link, for example via a radio link or via a cable. The remote control unit 6 can have a keyboard, but it is likewise possible for the remote control unit 6 to be in the form of a touchscreen. The remote control unit 6 is coupled to the control device 7 in the lower limb part 2 via a pairing process. For example, data relating to the basic functions of the controller for the prosthetic knee joint 4 are stored in the control device 7. Furthermore, control data for additional modes, for example descending stairs, riding a bike or sitting down are stored. These data for the so-called additional modes can be adjusted via the remote control unit 6. The scope of adjustment is in this case dependent, inter alia, on who the user of the remote control unit 6 is. The user of the prosthetic is provided with restricted rights in comparison with an orthopedic technician and can only change various parameters of the resistance changes within certain limits. For example, the degree of flexion damping in the momentum phase can be matched to the individual requirements. It is likewise possible to deactivate or activate additional modes individually, with it being possible to activate the additional modes such that they are implemented currently, but it is likewise possible to enable the additional modes via the remote control unit 6, i.e. to provide the principal possibility of activation, with the result that the respective program is activated automatically by the controller once corresponding sensor data are present.

The relevant data can be assigned to the respective remote control unit 6 by the control device in the lower limb part 2, with the result that easy and user-friendly assignment to the respective joint and the respective controller can take place, for example, via graphic symbols, so-called icons. The remote control unit 6 can supply a plurality of joints in a prosthetic, but it is likewise possible for a plurality of possibly different prosthetics with a plurality of possibly different joints and therefore also with a plurality of control devices to be supplied individually or jointly via a remote control unit 6, with the result that an orthopedic technician can manage a plurality of patients using one remote control unit 6, with the result that parameters can be changed by the orthopedic technician, for example during walking. Provision is also made for a patient to be able to adjust a plurality of possibly different orthopedic devices using one remote control unit 6. In this case, the rights of the orthopedic technician are more extensive than those of the user of the prosthetics since the orthopedic technician generally has greater knowledge of the background and the matching of the resistance device for the orthosis or prosthetic.

The invention claimed is:

1. A system,. comprising:
   at least one orthopedic device, comprising:
   at least one joint;
   a resistance device associated with the at least one joint;
   a control device;
   an actuator associated with the resistance device;
   wherein the actuator operates to move the at least one joint or adjust a resistance to at least one of a bending movement and a stretching movement;
   a remote control unit coupled to the control device and via which the resistance is adjusted;
   wherein data for operation of the remote control unit is stored in the orthopedic device, said data being used to configure the remote control unit for use in controlling the at least one orthopedic device, and said data being transmitted to the remote control unit via a pairing process.

2. The system as claimed in claim 1, wherein the orthopedic device further comprises a transmitter and the remote control unit further comprises a receiver.

3. The system as claimed in claim 1, wherein the orthopedic device further comprises various control modes stored in the control device, the control modes being activated and deactivated via the remote control unit.

4. The system as claimed in claim 1, wherein data relating to at least one of control parameters, control modes, language, arrangement of buttons, key assignments and adjustment ranges are stored in the orthopedic device.

5. The system as claimed in claim 1, wherein the remote control unit is designed to address a plurality of control devices or a plurality of joints.

6. The system as claimed in claim 1, wherein the user of the orthopedic device has restricted rights and adjustment possibilities in comparison with an orthopedic technician.

7. The system as claimed in claim 1, wherein the remote control unit is designed for switching over between a plurality of joints or control devices for the joints.

8. The system as claimed in claim 1, wherein the remote control unit is designed to at least one of switch over between a plurality of control modes and enable functions.

9. The system as claimed in claim 1, wherein the control device can be at least one of switched into and withdrawn from a deep-sleep mode via the remote control unit.

10. The system as claimed in claim 1, wherein a user identification is assigned to the remote control unit and is used to define at least one of which parameters and to what extent parameters can be adjusted in user-dependent fashion.

11. The system as claimed in claim 10, wherein the user identification is in the form of a code which can be input.

12. The system as claimed in claim 10, wherein the remote control unit has a detection device for biometric data, via which a user identification is assigned.

13. A system, comprising:
    at least one orthopedic device, comprising:
    at least one joint;
    a resistance device operable to apply resistance to the at least one joint;
    an actuator operable to move the at least one joint or adjust a resistance to at least one of a bending movement and a stretching movement via operation of the resistance device;
    a control device operable to control the actuator;
    a remote control unit coupled to the control device, wherein data for operation of the remote control unit is stored in the orthopedic device, said data is used to configure the remote control unit for use in controlling the at least one orthopedic device, and said data being transmitted from the control device to the remote control unit via a pairing process.

14. The system as claimed in claim 13, wherein the orthopedic device further comprises a transmitter and the remote control unit further comprises a receiver.

15. The system as claimed in claim 13, wherein the orthopedic device further comprises various control modes stored in the control device, the control modes being activated and deactivated via the remote control unit.

16. The system as claimed in claim 13, wherein data relating to at least one of control parameters, control modes, language, arrangement of buttons, key assignments and adjustment ranges are stored in the orthopedic device.

17. The system as claimed in claim 13, wherein the remote control unit is designed to communicate with a plurality of control devices or a plurality of joints.

18. The system as claimed in claim 13, wherein the user of the orthopedic device has restricted rights and adjustment possibilities in comparison with an orthopedic technician.

19. The system as claimed in claim 13, wherein the remote control unit is designed for switching over between a plurality of joints or control devices for the joints.

20. The system as claimed in claim 13, wherein the remote control unit is designed to at least one of switch over between a plurality of control modes and enable functions.

\* \* \* \* \*